United States Patent [19]

Mori

[11] Patent Number: 4,953,549
[45] Date of Patent: Sep. 4, 1990

[54] LIGHT RADIATOR

[76] Inventor: Kei Mori, 3-16-3-501, Kaminoge, Setagaya-ku, Tokyo, Japan

[21] Appl. No.: 412,357

[22] Filed: Sep. 25, 1989

[30] Foreign Application Priority Data

Jan. 18, 1989 [JP] Japan .................. 64-19427

[51] Int. Cl.⁵ .............................................. A61N 5/06
[52] U.S. Cl. ................................ 128/398; 128/395; 250/227.11; 350/96.24; 350/96.1; 362/32
[58] Field of Search ............. 128/393, 395, 396, 397, 128/398; 250/227; 350/96.1, 96.24; 362/32

[56] References Cited

U.S. PATENT DOCUMENTS

| | | | |
|---|---|---|---|
| 3,956,587 | 5/1976 | Nelson | 350/96.24 |
| 4,375,380 | 3/1983 | Genequand et al. | 350/96.24 |
| 4,743,082 | 5/1988 | Mori | 350/96.1 |
| 4,750,797 | 6/1988 | Mori | 350/96.1 |
| 4,820,015 | 4/1989 | Mogi | 350/96.24 |
| 4,838,271 | 6/1989 | Mori | 128/398 |

Primary Examiner—Lee S. Cohen
Assistant Examiner—Krista M. Pfaffle
Attorney, Agent, or Firm—Jordan and Hamburg

[57] ABSTRACT

A light radiator has a tubular body bearing at the center of one end a removable light-emitting end of a fiber optic cable and having at the other end a large number of light-guiding rods arranged tightly and parallel to each other. The light-guiding portion includes two groups of light-guiding rods, the first group consisting of rods having their light-emitting end-surfaces on the same plane and the second group consisting of rods having their end-surfaces on a plane lower than that of the first group's rods. Each light-guiding rod of the first group and each light-guiding rod of the second group are in contact with each other at least on one side and each light-guiding rod of the second group has a tapered, concave-shaped output end.

5 Claims, 3 Drawing Sheets

LIGHT RADIATOR

BACKGROUND OF THE INVENTION

The present invention relates to a light radiator which can receive solar rays, preferably containing only visible-spectrum components, from a fiber optic cable and effectively radiate the same onto a living body such as a horse or the like so as to stimulate the body's life-giving activity.

The present applicant has previously proposed focusing sunlight or artificial light rays by the use of lenses or the like and to guide them into a fiber optic cable in order to transmit them therethrough to wherever the light is needed for illumination or for other purposes, as for example to cultivate plants, chlorella, fish etc. As a result of doing research, it was found that visible light rays not containing therein ultraviolet and infrared rays are effective not only to promote health and prevent people's skin from aging but also to noticeably aid in healing such diseases as gout, neuralgia, bedsores, rheumatism, burns, skin diseases, injuries and bone fractures and in relieving pain from such diseases. Furthermore, on the basis of the above-mentioned inventor's discovery, the applicant has previously proposed a light radiation device for radiating visible light rays which correspond to the visible-spectrum components of sunlight and that do not contain therein harmful ultraviolet and infrared rays. The light rays can be used to give various kinds of medical and beauty treatments and to promote general health.

SUMMARY OF THE INVENTION

It is an object of the present invention to provide a light radiator which is suitable for radiating visible light rays onto cows, horses and other like animals to improve the blood flow in their skin through the action of the light.

It is another object of the present invention to provide a light radiator which can receive solar rays containing only visible-spectrum components from a fiber optic cable and effectively radiate the same onto a living body such as a horse or the like so as to stimulate the body's life-giving activity.

It is another object of the present invention to provide a light radiator which is capable of radiating visible-spectrum light rays transmitted by a fiber optic cable onto the surface of an animal's skin which has a coat of fur such as a horse, a cow etc., in order to promote the health of the animal, to heal an injury or a scar and to improve its coat of fur.

BRIEF DESCRIPTION OF THE DRAWINGS

(FIG. 1 is a sectional view taken on line I—I in FIG. 2.)

DESCRIPTION OF THE PREFERRED EMBODIMENTS

Figure 1:
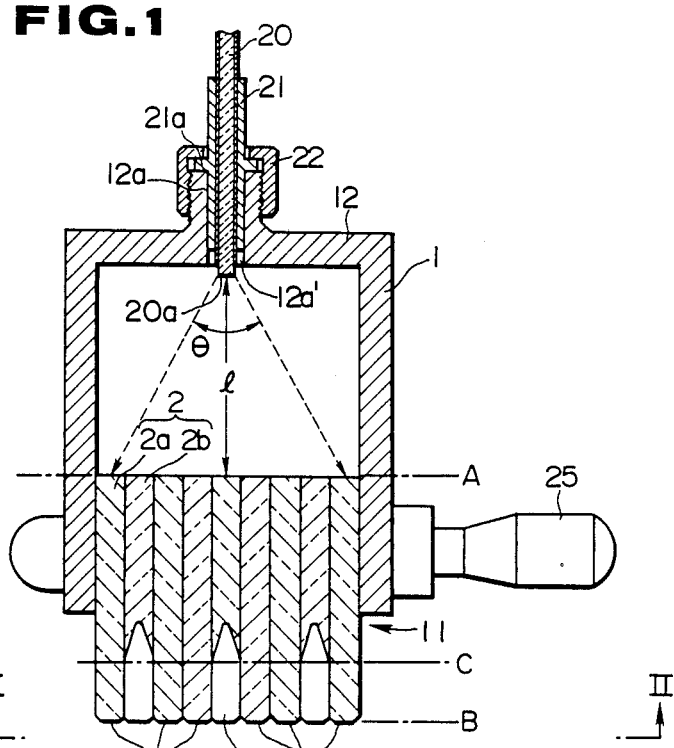
FIG. 1 is a sectional side view for explaining a light radiator as embodied in the present invention.
Figure 2:
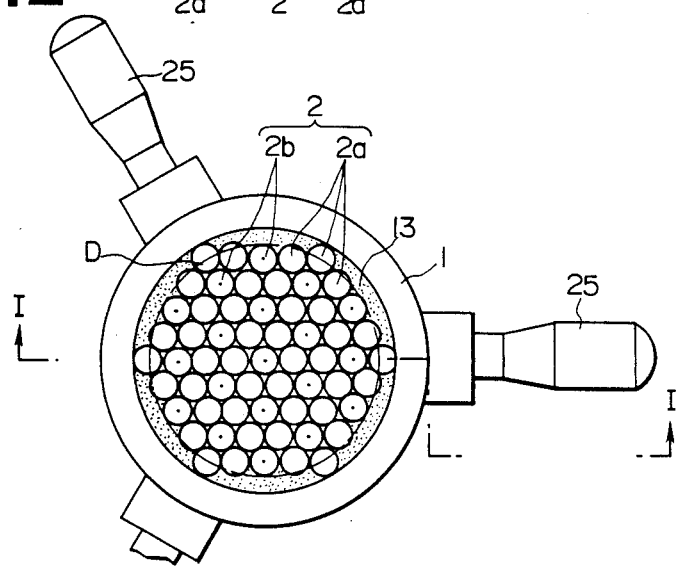
FIG. 2 is a plan view taken from line II—II in FIG. 1.

FIGS. 1 and 2 are construction views for explaining a light radiator embodying the present invention. FIG. 1 is a sectional side view taken on line I-I in FIG. 2, while FIG. 2 is a plan view taken of the light-radiator's surface (a view taken on line II—II in FIG. 1). In FIGS. 1 and 2, numeral 1 designates a tubular body made of an opaque resin or of a metal, where one end 11 is open and the other end 12 is formed as the bottom. A large number of light-guiding rods 2 made of transparent glass or acrylic resin are tightly inserted into the open end of the tubular body 1 and fixed therein by means of a resin 13 in such a way that they are aligned parallel to the axis of the tubular body 1. The light-guiding rods 2 are divided into two groups, that is, a first-group of light-guiding rods 2a and a second-group of light-guiding rods 2b. These light-guiding rods 2a and 2b have their input (light-receiving) end-surfaces A formed on the same plane but are different from each other in length and in the form of their other ends. Namely, the light-emitting end-surfaces of the first group's light-guiding rods 2a are placed on the same plane B, while the output ends of the second group's light-guiding rods 2b terminate at a plane C that is shorter than the plane B of the first-group's rods 2a and each light-guiding rod 2b has a tapered, concave-shaped output end 2b'. Numeral 20 is a fiber optic cable which is connected at its input end (not shown in FIGS. 1 and 2) to a solar ray collecting device as described below and which transmits therethrough the visible-spectrum components (white light) selected from the sunlight collected by the solar ray collecting device. 21 is a terminal sleeve for the fiber optic cable 20, and 22 is a cap nut which was previously put on a setting stopper 21a of the terminal sleeve 21 to be put on the output end of the fiber optic cable 20. 12a is a threaded portion provided at the center portion of the bottom side 12 of the tubular body 1 and which has a center port 12a' for mounting therein the terminal sleeve 21 with the output end of the fiber optic cable 20. The output end of the fiber optic cable 20 can be fixed in the tubular body 1 by inserting the terminal sleeve 21 with the cable's output end into the center port 12a' and then by screwing the cap nut onto the threaded portion 12 to clamp the stopper 21a of the sleeve 21 against the end-face of the threaded portion 12a of the tubular body 1. However, the method for fixing the output end of the fiber optic cable 1 to the tubular body 1 is not limited to that described above and any other known fixing means may also be used. Since the light transmitted through the fiber optic cable 20 is emitted usually at an angle θ of about 45° from the output end 21a of the cable 20, the light-receiving end-surface A of the light-guiding rods are preferably arranged within the limit of said light-emitting angle i.e. the distance "l" between the light-emitting end-surface 20a of the fiber optic cable 20 and the light-receiving end-surface A of the light-guiding rods 2 is preferably determined so as to be totally covered with the light as shown by the one-dot chain line D in FIG. 2. Since the level of the end-surface A of the light-guiding rods 2 in the tubular body 1 and the length of the threaded portion 12a of the tubular body 1 have already been fixed in the process of manufacturing the device, the relationship between the light-emitting end 20a of the fiber optic cable 20 and the light-receiving end-surface A of the light guiding rods will be automatically fixed at the time of mounting the fiber optic cable 20 in the tubular body 1 if the distance from the stopper 21a of the terminal sleeve 21 to the light-emitting end 20a of the fiber optic cable 20 has been preset.

Figure 3:
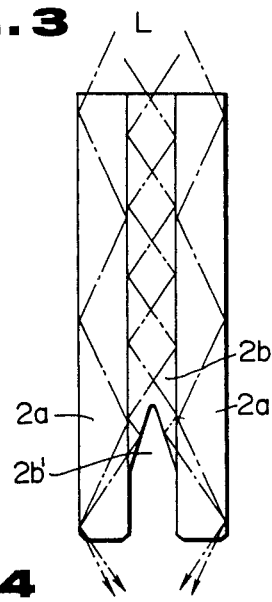
FIG. 3 is a view for explaining the correlation between a light-guiding rod 2a and a light-guiding rod 2b.

Accordingly, the light emitted from the light-emitting end 20a of the fiber optic cable 20 enters into the light-receiving end-surface A of the light-guiding rods at an incident angle of not more than 22.5°. Since the numerical aperture of the light-guiding rods 2 (maximum angle of incidence of the light to be propagated through the light-guiding rods) is also about 22.5°, almost all the light rays emitted from the end 2a of the fiber optic cable 20, except for reflected rays, can enter into the light-guiding rods 2. As shown in FIG. 3, the light rays "L" thus introduced into the light-guiding rods 2a propagate there-through and then are emitted from the light-emitting end-surface (B in FIG. 1). On the other hand, the light rays introduced into the light-guiding rods 2b propagate there-through and then are reflected at the inclined surfaces of the tapered concave-shaped ends 2b' (at the end-surface C in FIG. 1) so as to enter into the light-guiding rods 2a and be radiated from the light-emitting end-surface B.

In the light radiator, according to the present invention, the light-guiding rods 2a of the first group project far from the end-surface plane C of the light-guiding rods 2b of the second group and a clearance 2' is created thereby between the light-guiding rods 2a of the first group at their end-surface plane B. When the light radiator is laid on the skin's surface of a horse, the end-surfaces B of the light-guiding rods 2a may directly touch the horse's skin while accommodating a part of the fur in the clearances 2' and therefore the light from the ends of the light-guiding rods 2a is directly radiated onto the horse's skin. Furthermore, the light radiator can be used as a comb to groom the horse's fur and to improve its health.

In the embodiment described above, each light-guiding rod has a cylindrical form. However, it is well known that if a heat shrinkable tube containing therein a bundle of a large number of cylindrical light-guiding rods is heated, the cylindrical light-guiding rods are transformed into hexagonal light-guiding rods in close contact with each other. Accordingly, it is easily recognized that the end-surfaces of the light-guiding rods at the input side A are not always needed to have a cylindrical form and they may be formed into a hexagon by applying the above-mentioned method. The application of the hexagonal light-guiding rods may reduce the loss of the light energy transmitted since said rods, in comparison with cylindrical rods, can be more closely arranged together at the light-receiving side A. Furthermore, in the case of using hexagonal light-guiding rods, it is preferable to use a tubular body having a hexagonal cross-section instead of the cYlindrical body shown in FIGS. 1 and 2. The ends 2b' of the second group's light-guiding rods 2b are made of a conical, concave-shaped form. However, the concave-shaped portion 2' of each light guiding rod 2b may have a curved surface and practically be made in a form most suitable for the transfer of light therefrom into the light-guiding rod 2a. For easy handling of the light radiator three holding handles 25 are provided at the circumference of the tubular body 1. However, the number of handles may be changed.

As described above, the light radiator according to the present invention is suitable for use, in particular, for promoting the health of racing horses and for improving their coat of fur. Of course it can also be applied effectively to other animals. Since a horse is sensitive to bright light, the light radiator for a horse must have a tubular body made of an opaque material and must be fitted snugly onto the horse's body.

A light radiator for radiating the visible-spectrum components of sunlight was described above but an artificial source of light may also be used with it, corresponding to white light whenever solar rays cannot be collected as for instance, during the rainy season. In the case shown, the second group of light-guiding rods 2b are surrounded by the first group of light-guiding rods 2a. However, it is also possible to make an arrangement of the light-guiding rods of two groups in reverse to the one shown or in other variations without departing from the spirit of the present invention.

Figure 4:
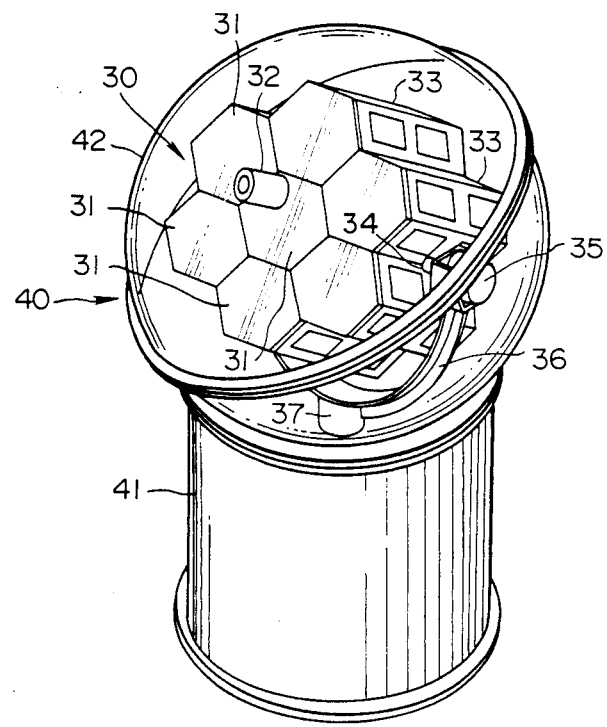
FIG. 4 is a view showing, by way of example, a solar ray collecting device to be preferably used in the embodiment of the present invention.

FIG. 4 is an entire perspective view illustrating an embodiment of the afore-mentioned solar ray collecting device. In FIG. 4, a capsule 40 for use in the solar ray collecting device is constructed as a cylindrical body 41 and a transparent dome-shaped head 42. As shown in FIG. 4, the solar ray collecting device 30 is accommodated in the capsule 40 while the device 30 is being used. The solar ray collecting device 30 comprises one lens, several lenses or possibly large numbers of lenses 31, a solar position sensor 32 for detecting the sun's location, a support-frame body 33 for integrally holding the lens system 31 and a sensor 32, a first-revolution shaft 34 for rotating the support frame 33, a first motor 35 for rotating the first revolution shaft 34, a supporting arm 36 for supporting the lens system 31, the sensor 32, the supporting frame body 33, the first revolution shaft 34 and the first motor 35, a second-revolution shaft 37 installed so as to intersect the first revolution shaft 34, a second-motor (not shown in FIG. 4) for rotating the second revolution shaft. The direction of the sun is detected by the solar position sensor 32 and its detection signal controls the first and second motors so as to direct the lens system 31 toward the sun, and the sunlight focused through each lens 31 is guided into the fiber optic cable (not shown in FIG. 4) through its light-receiving end-surface set at the focal point of the lens. The guided light rays are transmitted through the fiber optic cable onto a desired place.

Figure 5:
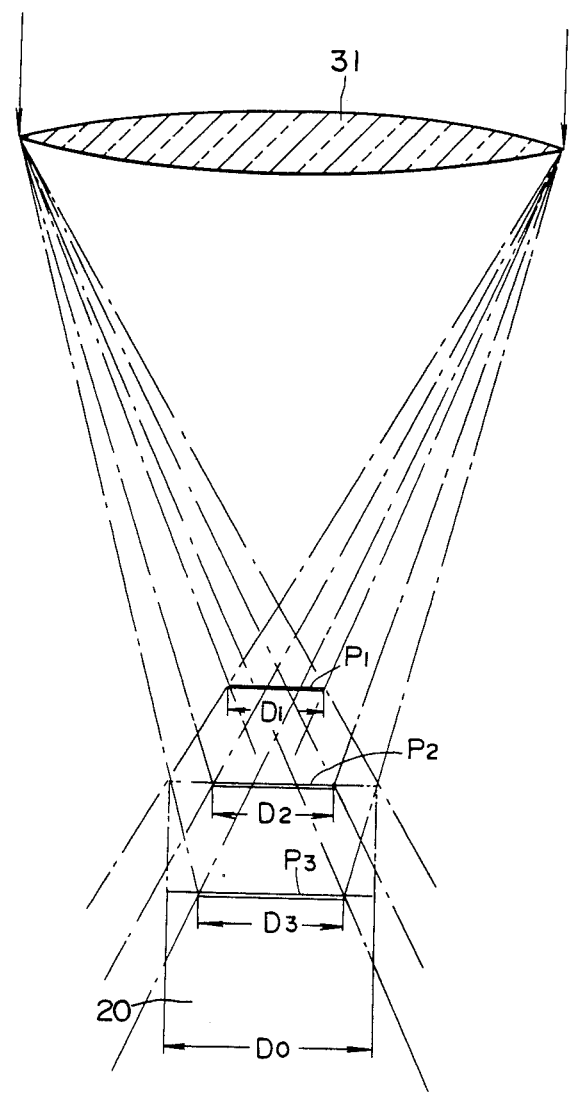
FIG. 5 is a view for explaining how to guide the visible light rays (visible-spectrum components of the light) into a fiber optic cable.

FIG. 5 is a view for explaining an embodiment for guiding the light ray corresponding to the visible-spectrum components of the (white) sunlight into a fiber optic cable.

In FIG. 5, 31 is a lens system consisting of a Fresnel lens (corresponding to the lens 31 shown in FIG. 4 or the like, and 20 is a fiber optic cable (corresponding to the fiber optic cable 20 shown in FIG. 1) for receiving the sunlight focused by the lens 31 and for transmitting the same therethrough. In the case of focusing the sunlight by using a lens system, the solar image has a central portion consisting of almost white light and a circumferential portion containing therein a large amount of light components of the wavelengths corresponding to the focal point of the lens system. Namely, in the case of focusing the sunlight through the lens system, the focal point and the size of the solar image will vary in accordance with the component wavelength of the light. For instance, the blue color light having a short wavelength makes a solar image of the diameter D1 at the position P1. Furthermore, the green color light makes a solar image of the diameter D2 at the position P2 and the red color light makes a solar image of the diameter D3 at the position P3.

Consequently, as shown in FIG. 5, when the light-receiving end-surface of the fiber optic cable is set at the position P1, it is possible to collect the sunlight containing plenty of the blue color component at the circumferential portion thereof. When the light-receiving end-surface of the fiber optic cable is set at the position P2, it is possible to collect sunlight containing plenty of the green color component at the circumferential portion thereof. When the light-receiving end-surface of the fiber optic cable is set at the position P3, it is possible to collect sunlight containing plenty of the red color component at the circumferential portion thereof. In each case, the diameter of the fiber optic cable can be selected in accordance with the light ray components to be collected. For instance, the required diameters of the fiber optic cables are D1, D2 and D3 respectively, depending upon the colors of the light rays to be stressed, i.e. the blue, green and red colors. In such a way, only the required amount of the fiber optic cable can be used and thereby the sunlight containing therein plenty of the desired color component can be collected most effectively. And further, as shown in FIG. 5, if the diameter of the light-receiving end of the fiber optic cable is enlarged to D0, it is possible to collect visible light containing therein all of the wavelength components.

As is apparent from the foregoing description, according to the present invention, it may be possible to provide a light radiator which is capable of radiating visible-spectrum (white) light rays transmitted by a fiber optic cable onto the surface of an animal's skin which has a coat of fur such as a horse, a cow etc., in order to promote the health of the animal, to heal an injury or a scar and to improve its coat of fur.

I claim:

1. A light radiator comprising a tubular body having opposite ends, fiber optical cable means for transmitting light rays mounted on one of said ends of said tubular body, said fiber optical cable means having a light-emitting end, a plurality of parallel light-guide rods disposed at the other of said ends of said tubular body, said plurality of light-guide rods receiving said light rays transmitted from said light-emitting end of said optical cable means, said plurality of light-guide rods comprising first and second groups of light-guide rods, said first group having light-emitting ends disposed in a first plane, said second group having light-emitting ends disposed in a second plane, said first plane being located further from said one of said ends of said tubular body than said second plane, each of said light-guide rods of said first group being in contact with one of said light-guide rods of said first group being in contact with one of said light-guide rods of said second group, said light-emitting ends of said second group of light-emitting rods having a tapered concave configuration.

2. A light radiator according to claim 1, wherein said plurality of light-guide rods of said first group are disposed about each of said plurality of light-guide rods of said second group.

3. A light radiator according to claim 1, wherein said plurality of light-guide rods of said second group are disposed about each of said plurality of light-guide rods of said first group.

4. A light radiator according to claim 1, wherein said tubular body is made of a non-transparent material.

5. A light radiator according to claim 1, further comprising at least one handle on said tubular body.

* * * * *